United States Patent [19]

Freerks et al.

[11] 4,092,332
[45] May 30, 1978

[54] PROCESS FOR MANUFACTURING MALEIC ANHYDRIDE

[75] Inventors: Marshall C. Freerks; Seth Randle, Sr., both of St. Louis, Mo.

[73] Assignee: Monsanto Company, St. Louis, Mo.

[21] Appl. No.: 701,765

[22] Filed: Jul. 2, 1976

Related U.S. Application Data

[63] Continuation-in-part of Ser. No. 351,402, Sep. 16, 1973, abandoned.

[51] Int. Cl.$^2$ ............................................. C07D 307/60
[52] U.S. Cl. ................................. 260/346.75; 252/437
[58] Field of Search ..................... 260/346.8 A, 346.75

[56] References Cited

U.S. PATENT DOCUMENTS

| 2,154,079 | 4/1939 | Weiss | 260/346.4 |
| 3,706,105 | 11/1964 | Kerr | 260/346.8 |
| 3,888,886 | 6/1975 | Young et al. | 260/346.8 |

Primary Examiner—Henry R. Jiles
Assistant Examiner—Bernard Dentz
Attorney, Agent, or Firm—J. C. Logomasini; F. L. Passley; S. M. Tarter

[57] ABSTRACT

The process for the conversion of saturated hydrocarbons having from 4 to 10 carbon atoms to maleic anhydride is enhanced when a mixture of oxygen and saturated hydrocarbon is contacted with catalysts comprising phosphorus, vanadium, oxygen and an element selected from the group consisting of titanium, silicon, or mixtures of these elements. The process is particularly useful for the conversion of butane to maleic anhydride.

5 Claims, No Drawings

PROCESS FOR MANUFACTURING MALEIC ANHYDRIDE

CROSS-REFERENCE TO RELATED APPLICATIONS

This application is a continuation-in-part of patent application Ser. No. 351,402 filed Apr. 16, 1973 now abandoned.

BACKGROUND OF THE INVENTION

1. FIELD OF THE INVENTION

This invention relates to a process for the manufacture of dicarboxylic acid anhydrides by the oxidation of hydrocarbons. More particularly, it is directed to a process suitable for producing maleic anhydride from saturated hydrocarbons in higher yields than heretofore possible.

Maleic anhydride is of significant commerical interest throughout the world. It is used alone or in combination with other acids in the manufacture of alkyd and polyester resins. It is also a versatile intermediate for chemical synthesis. Significant quantities of maleic anhydride are produced each year to satisfy these needs.

The prior art discloses a number of processes used in the conversion of organic feedstocks to maleic anhydride. As an example, U.S. Pat. No. 3,156,705 discloses the conversion of olefins to maleic anhydride using a phosphorus-vanadium-oxygen catalyst having a phosphorus to vanadium ratio varying from 1:1 to 2:1 wherein the phosphorus is stabilized with 0.05 to 5 weight percent titanium tetrachloride to prevent phosphorus loss from the catalysts during the conversion of the olefins to maleic anhydride. U.S. Pat. No. 3,156,706 discloses a process for the conversion of olefins to maleic anhydride using a vanadium-phosphorus-oxygen catalyst which contains from 0.05 to 5 weight percent of a mixture of an alkali metal and titanium to stabilize the phosphorus in the catalyst during the conversion. Both of these patents disclose that the vanadium in the catalyst was reduced to an average valence in the range of 2.5 to 4.6 using an acid such as hydrochloric acid or oxalic acid during the preparatory steps.

A process of oxidizing saturated aliphatic hydrocarbons to maleic anhydride under controlled temperature conditions in the presence of phosphorus-vanadium-oxygen catalysts was disclosed in U.S. Pat. No. 3,293,268. One method taught in that patent for preparing catalysts comprised reacting phosphoric acid with a vanadium compound in aqueous hydrochloric acid solution, recovering the remaining solids by evaporating the solution to dryness, and then heating the solids to 300° to 500° C. The resulting catalysts were ground to pass a 20 mesh screen and pelletted to form tablets. The tablets were then charged to a fixed catalyst bed in a test reactor at room temperature and the reactor heated for 16 hours. Thereafter, a 0.5 volume percent butane-in-air mixture was passed through the catalyst in a fixed tube reactor at temperatures above 400° C. to form maleic anhydride.

Despite the teachings in these and other references in the prior art, these teachings fail in one or more ways to achieve the results and advantages of the present invention. Although yields in excess of 20 mole percent were reported in U.S. Pat. No. 3,293,268, these yields were achieved only at temperatures between 500° and 600° C. and when using low butane concentrations in air. At temperatures below about 500° C., the yields of maleic anhydride were reported to be less than about 12 mole percent. On the other hand, the process of the present invention can convert butane to maleic anhydride in significant yields at temperatures as low as 350° C. using much stronger butane-in-air concentrations. The yields at lower operating temperatures that are achieved using the present process show that the present process is far superior to the prior art processes.

Although many workers in the prior art have disclosed processes using phosphorus-vanadium-oxygen catalysts deposited on an inert diluent, such as titania, for use in a fluidized bed or fixed tube reactor, improved yields or lower operating temperatures were not reported due to the presence of these elements, since they were usually present only as diluents and did not increase the activity of the catalysts. In stark contrast, however, to the prior art processes, the process of this invention is characterized by the conversion of saturated hydrocarbons to maleic anhydride at lower temperatures than heretofore possible.

SUMMARY OF THE INVENTION

It is an object of this invention to provide an improved process for preparing maleic anhydride. It is another object to provide an improved process for converting saturated hydrocarbons to maleic anhydride. It is another object to provide an improved process particularly suitable for converting butane to maleic anhydride.

These and other objects are achieved in a process for preparing maleic anhydride wherein a mixture of an oxygen-containing gas and a saturated hydrocarbon having from 4 to 10 carbon atoms is contacted with a catalyst, the improvement which comprises contacting the mixture of oxygen-containing gas and hydrocarbon at a temperature between about 350° and about 600° C. with a catalyst prepared from a precursor comprising phosphorus, vanadium, oxygen and a component selected from the group consisting of elements of titanium, silicon and mixtures thereof wherein the phosphorus to vanadium atom ratio is in the range of about 1:2 to about 2:1, the component to phosphorus atom ratio is between about 0.01:1 and about 0.2:1, and at least 50 atom percent of the vanadium is in the tetravalent state.

For the purposes of this invention, the term "catalytic activity" means the ability to convert a particular feedstock, such as butane, at a particular temperature to other compounds. The term "selectivity" means the ratio of the moles of maleic anhydride obtained to the moles of hydrocarbon reacted. The term "yield" means the ratio of the moles of maleic anhydride obtained to the moles of hydrocarbon introduced into the reaction. The term "space velocity" means the hourly volume of the gaseous feed expressed in cubic centimeters (cc) at 60° F. and standard atmospheric pressure divided by the catalyst bulk volume expressed in cubic centimeters (cc), the term expressed as cc/cc/hour.

Broadly described, the catalysts used in the process of this invention to convert saturated hydrocarbons to maleic anhydride are prepared by contacting vanadium compounds, phosphorus compounds, and a component containing at least one element selected from the group consisting of titanium, silicon and mixtures thereof, under such conditions that a substantial amount of tetravalent vanadium is provided to form catalyst precursors, recovering the catalyst precursors, forming the catalyst precursors into structures for use in a maleic anhydride reactor, and calcining the structured catalyst precursors to form the catalysts.

The vanadium compounds useful as a source of vanadium in the catalyst precursors are those known to the art to be useful for preparing catalysts to oxidize hydrocarbons. Suitable vanadium compounds include: vanadium oxides, such as vanadium pentoxide, vanadium trioxide, and the like; vanadium oxyhalides, such as vanadyl chloride, vanadyl trichloride, vanadyl dichloride, vanadyl bromide, vanadyl dibromide, vanadyl tribromide and the like; vanadium containing acids such as metavanadic acid, pyrovanadic acid and the like; vanadium salts, such as ammonia metavanadate, vanadium sulfate, vanadium phosphate, vanadyl formate, vanadyl oxalate and the like. However, vanadium pentoxide is preferred.

As a source of phosphorus in the catalyst precursors, useful phosphorus compounds are also those well known in the art useful for preparing catalysts to oxidize hydrocarbons. Suitable phosphorus compounds include: phosphoric acids, such as metaphosphoric acid, orthophosphoric acid, triphosphoric acid, pyrophosphoric acid, and the like; phosphorus oxides, such as phosphorus pentoxide and the like; phosphorus halides, such as phosphorus oxyiodide, phosphorus pentachloride, phosphorus oxybromide and the like; and organophosphorus compounds such as ethyl phosphate, methyl phosphate and the like. However, phosphoric acids, such as orthophosphoric acid and phosphorus pentoxide are preferred.

The compounds to provide the component of titanium for use in the catalyst precursors are also known to the art. However, it has been found that these compounds must be soluble, or at least partially soluble, in a strong mineral acid, such as hydrochloric acid, to be satisfactory for use in preparing the catalyst precursors. Suitable titanium compounds include: titanium halides, such as titanium dichloride, titanium trichloride, titanium tetrachloride, titanium dibromide, titanium tribromide, titanium tetrabromide, titanium diiodide, titanium triiodide, titanium tetraiodide, titanium tetrafluoride, potassium fluorotitanate and the like; inorganic titanates such as alkali metal titanates, alkaline earth metal titanates, aluminum titanate, lead titanate and the like; titanium salts such as titanium phosphates, titanium silicides, titanium silicates, titanium sulfates, and the like; alkyl titanates such as methyl titanate, ethyl titanate, isopropyl titanate, butyl titanate and the like; aryl titanates such as phenoxy titanium trichloride, phenyl titanate and the like. However, titanium tetrachloride and butyl titanate are preferred. Oxides, such as titanium dioxide, are not sufficiently soluble in a strong mineral acid, such as hydrochloric acid, and are not satisfactory for use in preparing the catalyst precursors although their presence is not harmful.

As a source of silicon in the catalyst precursors, useful silicon compounds are also those known to the art. Suitable silicon compounds include: silicon halides, such as silicon tetrachloride, silicon tetrabromide, silicon tetraiodide, hexabromodisilane, and the like; silicon esters of organic acids, such as silicon tetraacetate, and esters of ortho silicic acid such as tetraethoxysilane and the like. However, silicon tetrachloride is preferred.

To prepare precursors to the catalysts used in the present process, a pentavalent or tetravalent vanadium compound is heated with a phosphorus compound in an acid solution to dissolve the starting materials. A mild reducing agent is used to provide tetravalent vanadium and/or to maintain vanadium in the tetravalent state. On the other hand, an acid with reducing properties, such as a hydrogen halide acid or oxalic acid, can serve as the acid and can provide tetravalent vanadium. Hydrogen halides, such as hydrochloric acid, are preferred. The acid solution containing the phosphorus compound and the vanadium compound are heated until a blue solution is obtained, indicating that a substantial amount, i.e., greater than 50 atom percent, of the vanadium is in the tetravalent state. The amount of time required to dissolve the phosphorus and vanadium compounds and to provide a substantial amount of the vanadium in the tetravalent state to form the catalyst precursors varies from batch to batch, depending upon the compounds used as starting materials and the temperature at which the compounds are heated. However, as will occur to those skilled in the art, an aliquot of the solution can be analyzed to insure that most of the vanadium is in the tetravalent state.

Although any number of phosphorus compounds and vanadium compounds can be used to form the precursor, the atom ratio of phosphorus to vanadium in the precursor is important, since it controls the phosphorus to vanadium atom ratio in the final catalyst. When the precursor contains a phosphorus to vanadium atom ratio below about 1:2 or above about 2:1, the yield of maleic anhydride using the process of this invention is so low that it is not of commercial significance. It is preferred that the precursors have a phosphorus to vanadium atom ratio in the range of about 1:1 to about 1.5:1. When the catalyst is used to convert a feed that is primarily butane to maleic anhydride, it is even more preferable to have a phosphorus to vanadium atom ratio of about 1:1 to about 1.2:1, say about 1.1:1.

The component of titanium and/or silicon must be added to the phosphorus and vanadium mixture during the preparation of the precursor to insure that the elements become a part of the precursor, and it is preferable to add these components to the acid solution before the vanadium compound is added to the acid solution during the formation of the catalyst precursor.

The atom ratio of the component to phosphorus in the precursor is important since it affects the catalytic activity of the final catalyst. When the precursor contains a component to phosphorus atom ratio of less than about 0.05:1, the yield of maleic anhydride decreases, although the yield is still higher than if the component were not present at all. The yield is noticeably improved by a component to phosphorus atom ratio as small as 0.01:1. At a component to phosphorus atom ratio greater than 0.2:1, no additional benefit is seen, although the presence of higher concentrations of component is not harmful. It is preferred that precursors have a component to phosphorus atom ratio from about 0.05:1 to about 0.1:1.

After the precursors have been formed by heating the vanadium compounds and the phosphorus compounds along with compounds of titanium and/or silicon, and a substantial amount of the vanadium has been reduced to the tetravalent state, it is necessary to remove most of the water in order to recover the precursor. Techniques for recovering the precursors from solution are well known to those skilled in the art. Precursors can be deposited on a carrier, such as alumina or titania, from solution, or excess water can be removed to provide the precursors.

After the precursors are recovered from solution, they are then formed into structures suitable for use in a maleic anhydride reactor. Techniques for forming appropriate structures from the precursors for use in a fluidized bed reactor or in a fixed tube, heat exchanger type reactor are well known to those skilled in the art. For example, the precursors can be structured for use in a fluidized bed reactor by depositing the precursors from solution on a carrier, or alternatively, the dried precursors can be comminuted for use in a fluidized bed reactor. On the other hand, the precursors can be structured for use in a fixed tube reactor by prilling or tabletting the precursors.

After the precursors have been formed into the structures in which they will be used in the maleic anhydride reactor, they can be calcined in an inert atmosphere, such as nitrogen or a noble gas, at temperatures of from about 350° to about 600° C. for at least about 2 hours to convert the precursors to the catalysts for use in the present process.

In a preferred embodiment, the precursors are calcined in air up to a temperature of about 250° C. or until about 20 atom percent to about 80 atom percent of the vanadium has been oxidized to pentavalent vanadium, and then calcined at temperatures of from about 350° C. to about 500°–550° C. for at least 2 to 4 hours in an inert atmosphere. If more than about 80 atom percent of the vanadium is oxidized to pentavalent vanadium, usually caused by calcining in air at too high a temperature, the selectivity of the catalyst and the yield of maleic anhydride decrease markedly. On the other hand, oxidation of less than about 20 atom percent of the vanadium during air calcination does not seem to be more beneficial than calcination in an inert atmosphere.

After the precursors have been calcined to form the catalysts of this process, the catalysts can be used to convert a saturated hydrocarbon to maleic anhydride. However, the initial yield of maleic anhydride may be low, and if this is the case, the catalysts can be conditioned, as will occur to those skilled in the art by passing low concentrations of a saturated hydrocarbon in air at low space velocities through the catalyst for a period of time before production operations begin.

After the catalysts of the present process have been used about 16 hours to prepare maleic anhydride from a mixture of about 1.5 atom percent saturated hydrocarbon, such as butane, at a space velocity of about 1500 cc/cc/hour at a temperature of about 440° C., a substantial amount, i.e., greater than 50 atom percent of the vanadium in the catalyst is in the tetravalent state, as determined by the tetravalent vanadium test hereinafter described. When the catalysts contain less than about 50 atom percent vanadium in the tetravalent state, the catalyst is too unselective to be used for the oxidation of saturated hydrocarbons to maleic anhydride.

In the tetravalent vanadium test, a sample of the catalyst is dissolved in dilute sulfuric acid, and thereafter, the tetravalent vanadium is titrated with a standardized permanganate solution in a first titration. The pentavalent vanadium is then reduced to the tetravalent state by the addition of sodium sulfite and the vanadium is titrated with the standardized permanganate solution in a second titration. The percent tetravalent vanadium can be calculated from the differences between the two values.

The catalysts of the present process are useful in a variety of reactors to convert saturated hydrocarbons to maleic anhydride. Both fluidized bed reactors and fixed tube heat exchanger type reactors are satisfactory and details of the operation of such reactors are well known to those skilled in the art. The reaction to convert saturated hydrocarbons to maleic anhydride requires only contacting the saturated hydrocarbon admixed with a free-oxygen containing gas, such as air or oxygen-enriched air, with the catalysts at elevated temperatures. The saturated hydrocarbons are contacted with the catalysts at a concentration of about 1.5 to about 10 volume percent saturated hydrocarbons at a space velocity of about 100 to 4,000 cc/cc/hour to provide maleic anhydride yields of greater than 40% at temperatures between about 350° and 600° C.

The catalysts of the present process are particularly useful in fixed tube heat exchanger type reactors. The tubes of such reactors can vary in diameter from about ¼ inch to about 1.5 inches and the length can vary from about 6 inches to about 10 or more feet. It is desirable to have the surfaces of the reactors at relatively constant temperature, and some medium to conduct heat from the reactors is necessary to aid temperature control. Such media can be Woods metal, molten sulfur, mercury, molten lead and the like or eutectic salt baths. A metal block reactor whereby the metals surrounding the tube act as a temperature regulating body can also be used. The reactor or reaction tubes can be iron, stainless steel, carbon steel, glass and the like.

Maleic anhydride prepared by using the process of this invention can be recovered by any number of means well known to those skilled in the art. For example, the maleic anhydride can be recovered by direct condensation or by absorption in suitable media with subsequent separation and purification of the anhydride.

The pressure in the reactor is not generally critical. Therefore, the reaction can be run at atmospheric, superatmospheric and subatmospheric pressures, although superatmospheric pressures are usually employed.

A large number of saturated hydrocarbons having from 4 to 10 carbon atoms can be converted to maleic anhydride using the process of the present invention. It is only necessary that hydrocarbons contain not less than 4 carbon atoms in a straight chain. As an example, the preferred saturated hydrocarbon is butane, but isobutane which does not contain 4 carbon atoms in a straight chain is not satisfactory for conversion to maleic anhydride, although its presence is not harmful. In addition to butane, other saturated hydrocarbons within the scope of this invention include the pentanes, the hexanes, the heptanes, the octanes, the nonanes, the decanes, or mixtures of any of these with or without butane. In addition to the above compounds, cyclic compounds such as cyclopentane or cyclohexane are satisfactory feed materials for conversion to maleic anhydride. Also, the feedstock can be technical grade hydrocarbons containing up to about 25 weight percent of olefinically unsaturated hydrocarbons or other hydrocarbon fractions.

The principal product from the oxidation of the above feed materials is maleic anhydride. It should be noted that small amounts of citraconic anhydride may also be produced when the feedstock is a saturated hydrocarbon containing more than 4 carbon atoms.

DESCRIPTION OF THE PREFERRED EMBODIMENTS

In a preferred embodiment of this process, the catalyst is prepared by dissolving a compound of titanium and/or silicon in hydrochloric acid. The hydrochloric acid containing the dissolved compounds is then added to a mixture of phosphoric acid and hydrochloric acid in such proportions that the atom ratio of component to phosphorus is at least 0.05:1. Thereafter, vanadium pentoxide is added to the acid mixture in such proportions that the atom ratio of phosphorus to vanadium is slightly above 1:1. The acid mixture is then heated until tetravalent vanadium is provided to form the catalyst precursor.

The aqueous solution containing the precursor is evaporated to apparent dryness. Then, from about 10 to about 40 weight percent water is added to the precursor to form a putty. Alternatively, only so much of the water from the aqueous solution is removed as is necessary to form a viscous putty. The amount of water in the putty is not critical provided that there is sufficient water to permit forming into a suitable structure, such as by extrusion or pelletting, but not so much water as to cause the wet mixture to slump after it is formed. A putty containing less than about 10 weight percent water is difficult to extrude whereas a putty containing greater than about 40 weight percent water will normally slump and not hold its shape. However, it should be noted that various additives, such as a gelling agent or a lubricant, can be added to the putty that can change this ratio as will occur to those skilled in the art.

The putty of precursor and water can be structured by extruding the putty through a die, drying the extrudate, and dividing the extrudate into pellets or tablets. Alternatively, the extrudate can be divided into pellets before drying, and this latter procedure is preferred.

The structured precursor is then calcined by placing the structured precursor in an oven at room temperature and heating the precursor to about 250° C. in air. Thereafter, the air is replaced with nitrogen and the temperature increased to about 500° C. and maintained at the higher temperature for at least 2 hours. The catalyst is permitted to cool to room temperature in the nitrogen atmosphere. The resulting catalyst is then ready to be used in the maleic anhydride reactor.

This invention is further illustrated by, but not limited to, the following Examples.

EXAMPLES I – IX

The catalysts of this process were prepared by dissolving titanium tetrachloride, silicon tetrachloride, or mixtures thereof, in a small amount of 12 normal hydrochloric acid. This acid was then added to phosphoric acid and hydrochloric acid in such amounts that the atom ratio of the component to phosphorus is at least 0.05:1. Thereafter, vanadium pentoxide was added to the acid mixture so that the phosphorus to vanadium atom ratio was about 1.06:1. The solution was heated at reflux conditions until the vanadium was reduced to the tetravalent state. The resultant precursor was recovered by heating the solution to dryness. The remaining solid precursor was then slurried with about 20 weight percent water to form a viscous putty. The putty was then extruded through a die to produce an extrusion of about 7/32-inch diameter, which was then cut to form cylinders about 7/32-inch long. After these cylinders were allowed to air dry, they were then calcined up to about 250° C. in air, and then to 500° C. for 2 to 4 hours in nitrogen.

The calcined catalyst was then charged to a 1-inch outside diameter, iron, fixed tube reactor to a depth of about 6 inches. After 50 hours using a feed containing 3.5 percent butane-in-air, the data presented in Table I were obtained. Example I, given for comparative purposes, discloses the results obtained by a process wherein a component element was not added to the phosphoric acid-vanadium pentoxide mixture. These data using this reactor correlate well with the results that would be obtained in a production reactor.

TABLE I

| EXAMPLE | Atom Ratio Ti:P | Atom Ratio Si:P | Space Velocity (cc/cc/hour) | Bath Temp. (° C.) | Reaction Temp. (° C.) | Maleic Anhydride Yield (%) |
|---|---|---|---|---|---|---|
| 1 | — | — | 2700 | 449 | 527 | 28 |
| 2 | 0.09:1 | — | 2500 | 354 | 390 | 16 |
| 3 | 0.07:1 | — | 2500 | 385 | 425 | 23.5 |
| 4 | 0.07:1 | 0.02:1 | 2520 | 371 | 411 | 30.6 |
| 5 | 0.07:1 | 0.02:1 | 2550 | 381 | 441 | 29.8 |
| 6 | 0.03:1 | 0.02:1 | 2600 | 430 | 481 | 23.4 |
| 7 | 0.07:1 | 0.02:1 | 2500 | 370 | 410 | 24.0 |
| 8 | 0.07:1 | — | 2500 | 335 | 370 | 23.5 |
| 9 | 0.07:1 | 0.22:1 | 2500 | 358 | 393 | 22.2 |

Samples of catalysts from Examples I through IX were analyzed by the tetravalent vanadium test. In all cases, the catalysts contained greater than 50 percent tetravalent vanadium, and usually contained greater than 90 percent tetravalent vanadium.

EXAMPLES X – XII

These catalysts were prepared as in Examples I through IX except that the putty was extruded through a die to produce an extrusion of about 1/16-inch diameter which was then cut to form cylinders of about ¼-inch long. After calcination, the catalysts were charged to a ½-inch diameter, glass, fixed tube reactor to a depth of about 6 inches. The results obtained, which are presented in Table II, using this reactor correlate well with the results that would be obtained in a production reactor.

TABLE II

| Ex. | Atom Ratio Ti:P | Atom Ratio Si:P | Space Velocity (cc/cc/hour) | Bath Temp.[1] (° C.) | Maleic Anhydride Yield (%) |
|---|---|---|---|---|---|
| 10 | 0.08 | — | 3050 | 400 | 32.5 |
| 11 | 0.04 | 0.04 | 2800 | 410 | 32.6 |
| 12 | — | 0.1:1 | 2875 | 454 | 32.2 |

[1]Maximum temperature of metal block surrounding the glass reaction tube.

Although this invention has been described in terms of specified embodiments which are set forth in considerable detail, it should be understood that this is by way of illustration only, and that the invention is not necessarily limited thereto, since alternative embodiments and operating techniques will become apparent to those skilled in the art in view of the disclosure. Accordingly, modifications are contemplated which can be made without departing from the spirit of the described invention.

What is claimed is:

1. In a process for preparing maleic anhydride wherein a mixture of an oxygen-containing gas and a saturated hydrocarbon having from 4 to 10 carbon atoms is contacted with a catalyst, the improvement comprises contacting the mixture of oxygen-containing gas and hydrocarbon at a temperature between about 350° and about 600° C. with a catalyst prepared from an acid soluble precursor comprising phosphorus, vanadium, oxygen and a component selected from the group consisting of silicon and mixtures of silicon and titanium, wherein the phosphorus to vanadium atom ratio is in the range of about 1:2 to about 2:1, the component to phosphorus atom ratio is between about 0.05:1, and about 0.1:1, and at least 50 atom percent of the vanadium is in the tetravalent state.

2. In a process of claim 1 wherein the phosphorus to vanadium atom ratio is in the range of about 1:1 to about 1.5:1.

3. In a process of claim 1 wherein the phosphorus to vanadium atom ratio is in the range of about 1:1 to about 1.2:1.

4. In a process of claim 1 wherein the component is silicon.

5. In a process of claim 1 wherein the component is titanium and silicon.